(12) United States Patent
Nageri et al.

(10) Patent No.: US 11,045,656 B2
(45) Date of Patent: Jun. 29, 2021

(54) BIASED LEAD CONNECTOR FOR OPERATING ROOM CABLE ASSEMBLY AND METHODS OF MAKING AND USING

(71) Applicant: Boston Scientific Neuromodulation Corporation, Valencia, CA (US)

(72) Inventors: Ranjan Krishna Mukhari Nageri, Valencia, CA (US); Katie Hoose, Milpitas, CA (US); Alex Pruitt, Milpitas, CA (US); Dennis Johnson, Milpitas, CA (US); Maziyar Keshtgar, Milpitas, CA (US); Brian Fang, Milpitas, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 305 days.

(21) Appl. No.: 16/132,018

(22) Filed: Sep. 14, 2018

(65) Prior Publication Data

US 2019/0083794 A1    Mar. 21, 2019

Related U.S. Application Data

(60) Provisional application No. 62/559,195, filed on Sep. 15, 2017.

(51) Int. Cl.
*A61N 1/375* (2006.01)
*A61N 1/36* (2006.01)
(Continued)

(52) U.S. Cl.
CPC ............ *A61N 1/3752* (2013.01); *A61N 1/05* (2013.01); *A61N 1/0502* (2013.01); *A61N 1/36017* (2013.01); *A61N 1/37241* (2013.01)

(58) Field of Classification Search
None
See application file for complete search history.

(56) References Cited

U.S. PATENT DOCUMENTS

| 3,222,471 A | 12/1965 | Steinkamp |
| 3,601,747 A | 8/1971 | Prall et al. |

(Continued)

FOREIGN PATENT DOCUMENTS

| EP | 0580928 A1 | 2/1994 |
| EP | 0650694 B1 | 7/1998 |

(Continued)

OTHER PUBLICATIONS

International Search Report and Written Opinion for PCT Application No, PCT/US2018/051171 dated Dec. 19, 2018.

*Primary Examiner* — Kennedy Schaetzle
(74) *Attorney, Agent, or Firm* — Branch Partners PLLC; Bruce E. Black

(57) ABSTRACT

An operating room cable assembly for an electrical stimulation system that includes a lead connector having a housing, a lead lumen extending inwardly from a first opening in the housing and configured and arranged to receive a portion of a lead or lead extension, and a contact assembly disposed within the housing and configured and arranged to move relative to the housing. The contact assembly is configured and arranged to move to a load position and is biased to return to a lock position. The contact assembly includes of contacts that are configured and arranged to engage a portion of any lead or lead extension within the lead lumen when the contact assembly is in the lock position and to disengage from the portion of the lead or lead extension within the lead lumen when the contact assembly is in the load position.

20 Claims, 9 Drawing Sheets

(51) Int. Cl.
*A61N 1/05* (2006.01)
*A61N 1/372* (2006.01)

(56) References Cited

U.S. PATENT DOCUMENTS

| | | |
|---|---|---|
| 3,718,142 A | 2/1973 | Mulier |
| 3,757,789 A | 9/1973 | Shanker |
| 3,771,106 A | 11/1973 | Matsumoto et al. |
| 3,908,668 A | 9/1975 | Bolduc |
| 3,951,154 A | 4/1976 | Hartlaub |
| 3,990,727 A | 11/1976 | Gallagher |
| 4,003,616 A | 1/1977 | Springer |
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,942,876 A * | 7/1990 | Gotthardt ............ A61N 1/3752 439/817 |
| 4,951,687 A | 8/1990 | Ufford et al. |
| 4,995,389 A | 2/1991 | Harris |
| 5,000,177 A | 3/1991 | Hoffman et al. |
| 5,000,194 A | 3/1991 | van den Honert et al. |
| 5,007,435 A | 4/1991 | Doan et al. |
| 5,007,864 A | 4/1991 | Stutz, Jr. |
| 5,069,209 A * | 12/1991 | Posin .................. A61N 1/3752 439/837 |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A * | 10/1993 | Giurtino ............ H01R 4/4818 439/441 |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,582,180 A | 8/1996 | Manset et al. |
| 5,560,358 A | 10/1996 | Arnold et al. |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A * | 7/1998 | Castle .................. A61N 1/3752 607/37 |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A * | 8/1999 | Werner ................ A61N 1/3752 607/115 |
| 5,938,688 A | 8/1999 | Schiff |
| 5,951,595 A | 9/1999 | Moberg et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kest et al. |
| 6,018,684 A | 1/2000 | Bartig et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,161,047 A | 12/2000 | King et al. |
| 6,162,101 A | 12/2000 | Fischer et al. |
| 6,164,284 A | 12/2000 | Schulman et al. |
| 6,167,311 A | 12/2000 | Rezai |
| 6,167,314 A | 12/2000 | Fischer, Sr. et al. |
| 6,175,710 B1 | 1/2001 | Kamaji et al. |
| 6,181,969 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,271,094 B1 | 8/2001 | Boyd et al. |
| 6,295,944 B1 | 10/2001 | Lovett |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |

(56) References Cited

U.S. PATENT DOCUMENTS

| | | | |
|---|---|---|---|
| 6,473,654 B1 | 10/2002 | Chinn |
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Snits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,687,538 B1* | 2/2004 | Hrdlicka ............ A61N 1/36017 607/2 |
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,913,478 B2 | 7/2005 | Lamrey |
| 6,921,295 B2 | 7/2005 | Sommer et al. |
| 6,968,235 B2 | 11/2005 | Belden et al. |
| 6,980,863 B2 | 12/2005 | van Venrooij et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 | 2/2009 | Franz |
| 7,512,446 B2 | 3/2009 | Honeck |
| 7,516,447 B2 | 3/2009 | Drew |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,668,601 B2 | 2/2010 | Hegiand et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,140,172 B1 | 3/2012 | Jones et al. |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kest et al. |
| 8,527,054 B2 | 9/2013 | North |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,784,143 B2 | 7/2014 | Edgell et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,234,591 B2 | 1/2016 | Dilmaghanian et al. |
| 9,270,070 B2 | 2/2016 | Pianca |
| 9,289,596 B2 | 3/2016 | Leven |
| 9,352,147 B2 | 5/2016 | Nguyen-Stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,517,338 B1 | 12/2016 | Jiang et al. |
| 9,604,068 B2 | 3/2017 | Malinowski |
| 9,656,093 B2 | 5/2017 | Villarta et al. |
| 9,770,598 B2 | 9/2017 | Malinowski et al. |
| 9,855,413 B2 | 1/2018 | Vadlamudi et al. |
| 10,195,423 B2 | 2/2019 | Jiang et al. |
| 2001/0023368 A1 | 9/2001 | Black et al. |

(56) References Cited

U.S. PATENT DOCUMENTS

| | | |
|---|---|---|
| 2002/0143376 A1* | 10/2002 | Chinn ................. A61N 1/05 607/115 |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0230268 A1 | 11/2004 | Huff et al. |
| 2004/0260373 A1 | 12/2004 | Ries et al. |
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0035692 A1* | 2/2012 | Cantion ................ A61N 1/0558 607/116 |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0082254 A1 | 3/2016 | Moffitt et al. |
| 2016/0082255 A1 | 3/2016 | Moffitt et al. |
| 2016/0129242 A1 | 5/2016 | Malinowski |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0220826 A1 | 8/2016 | Funderburk |
| 2016/0228692 A1 | 8/2016 | Steinke et al. |
| 2016/0296745 A1 | 10/2016 | Govea et al. |
| 2016/0375238 A1 | 12/2016 | Leven et al. |
| 2017/0072187 A1 | 3/2017 | Howard et al. |
| 2017/0143978 A1 | 5/2017 | Barker |
| 2017/0203104 A1 | 7/2017 | Nageri et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0214687 A1 | 8/2018 | Nageri et al. |

(56) References Cited

U.S. PATENT DOCUMENTS

| | | |
|---|---|---|
| 2018/0243570 A1 | 8/2018 | Malinowski et al. |
| 2018/0289968 A1 | 10/2018 | Lopez |
| 2018/0369596 A1 | 12/2018 | Funderburk |
| 2019/0030345 A1 | 1/2019 | Funderburk |
| 2019/0083793 A1 | 3/2019 | Nageri |
| 2019/0083794 A1 | 3/2019 | Nageri |
| 2019/0103696 A1 | 4/2019 | Conger |

FOREIGN PATENT DOCUMENTS

| | | |
|---|---|---|
| EP | 0832667 B1 | 2/2004 |
| EP | 1181947 81 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |
| WO | 2016/077649 | 5/2016 |

* cited by examiner

BIASED LEAD CONNECTOR FOR OPERATING ROOM CABLE ASSEMBLY AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/559,195, filed Sep. 15, 2017, which is incorporated herein by reference.

FIELD

The present invention is directed to the area of implantable electrical stimulation systems and methods of making and using the systems. The present invention is also directed to a biased lead connector for an operating room cable assembly for use with an implantable electrical stimulation system, as well as methods of making and using the operating room cable assembly.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an operating room cable assembly for an electrical stimulation system that includes a lead connector having a housing, a lead lumen extending inwardly from a first opening in the housing and configured and arranged to receive a portion of a lead or lead extension, and a contact assembly disposed within the housing and configured and arranged to move relative to the housing. The contact assembly is configured and arranged to move to a load position and is biased to return to a lock position. The contact assembly includes of contacts that are configured and arranged to engage a portion of any lead or lead extension within the lead lumen when the contact assembly is in the lock position and to disengage from the portion of the lead or lead extension within the lead lumen when the contact assembly is in the load position.

In at least some embodiments, the operating room cable assembly further includes a button coupled to the contact assembly, disposed within the housing, and movable relative to the housing, wherein the button is configured and arranged to move the contact assembly to the load position when the button is pushed and to return the contact assembly to the lock position when the button is released. In at least some embodiments, the button includes a carriage and the contact assembly is fastened to the carriage. In at least some embodiments, the carriage includes a lead engagement portion that is configured and arranged to engage the portion of the lead or lead extension in the lead lumen when the contact assembly is in the lock position to facilitate retention of the lead or lead extension.

In at least some embodiments, the operating room cable assembly further includes an elongated body coupled to, and extending from, the lead connector and including conductors with each of the conductors coupled to at least one of the contacts of the contact assembly of the lead connector. In at least some embodiments, the operating room cable assembly further includes a trial stimulator connector coupled to the elongated body and including at least one contact coupled to the conductors of the elongated body.

In at least some embodiments, the operating room cable assembly further includes at least one spring disposed between the contact assembly and the housing and configured and arranged to bias the contact assembly to the lock position. In at least some embodiments, the operating room cable assembly further includes a lead lumen housing disposed within the housing and defining at least a portion of the lead lumen. In at least some embodiments, the lead lumen housing further defines a plurality of contact openings that intersect the lead lumen and through which the contacts of the contact assembly can move between the load position and the lock position.

In at least some embodiments, the operating room cable assembly further includes a stylet lumen inwardly extending from a second opening in the housing opposite the lead lumen and intersecting the lead lumen. In at least some embodiments, the operating room cable assembly further includes a visually distinctive marking disposed on the housing around the first opening. In at least some embodiments, the contacts are "M" shaped pins. In at least some embodiments, the contact assembly includes a base with the contacts attached to the base. In at least some embodiments, the button includes a carriage and the base is part of the carriage.

Another embodiment is a trial stimulation system that includes a trial stimulator; and any of the operating room cable assemblies described above and coupleable, or coupled, to the trial stimulator. The trial stimulation system optionally includes a lead coupleable to the lead connector of the operating room cable assembly. The trial stimulation system optionally includes a lead extension coupleable to the lead and the lead connector of the operating room cable assembly.

A further embodiment is an insertion kit that includes any of the operating room cable assemblies described above and at least one electrical stimulation lead, each electrical stimulation lead having a distal end portion and a proximal end portion and including electrodes disposed along the distal end portion of the electrical stimulation lead, terminals disposed along the proximal end portion of the electrical stimulation lead, and conductors coupling the electrodes to the terminals, where the proximal end portion of the electrical stimulation lead is insertable into the lead connector of the operating room cable assembly.

Yet another embodiment is a method for performing a trial stimulation on a patient. The method includes providing any of the operating room cable assemblies described above; advancing a distal end portion of an electrical stimulation lead into the patient with a proximal end portion of the electrical stimulation lead extending outward from the patient, wherein the distal end portion of the electrical stimulation lead is advanced to a position where a plurality of electrodes disposed along the distal end portion of the electrical stimulation lead are in proximity to a target stimulation location; placing the proximal end portion of the electrical stimulation lead into the lead connector of the operating room cable assembly while the contact assembly is in the load position; and allowing the contact assembly to return to the lock position to lock the proximal end portion of the lead in the lead connector.

Another embodiment is a method for performing a trial stimulation on a patient. The method includes providing any of the operating room cable assemblies described above; advancing a distal end portion of an electrical stimulation lead into the patient with a proximal end portion of the electrical stimulation lead extending outward from the patient, wherein the distal end portion of the electrical stimulation lead is advanced to a position where a plurality of electrodes disposed along the distal end portion of the electrical stimulation lead are in proximity to a target stimulation location; coupling the lead to a lead extension; placing a proximal end portion of the lead extension into the lead connector of the operating room cable assembly while the contact assembly is in the load position; and allowing the contact assembly to return to the lock position to lock the proximal end portion of the lead extension in the lead connector.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to a push-button lead connector for an operating room cable assembly for use with an implantable electrical stimulation system, as well as methods of making and using the operating room cable assembly.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
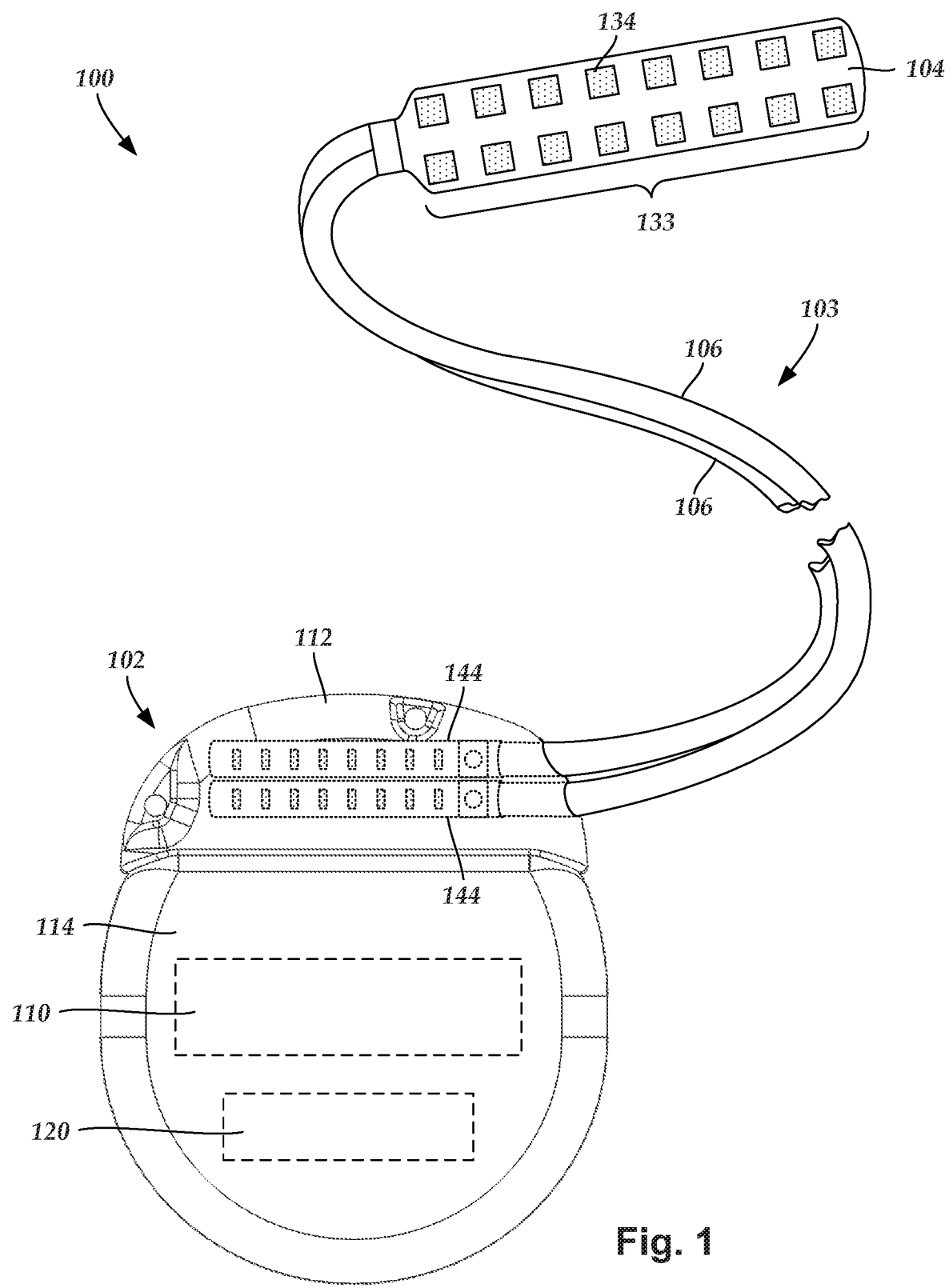
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
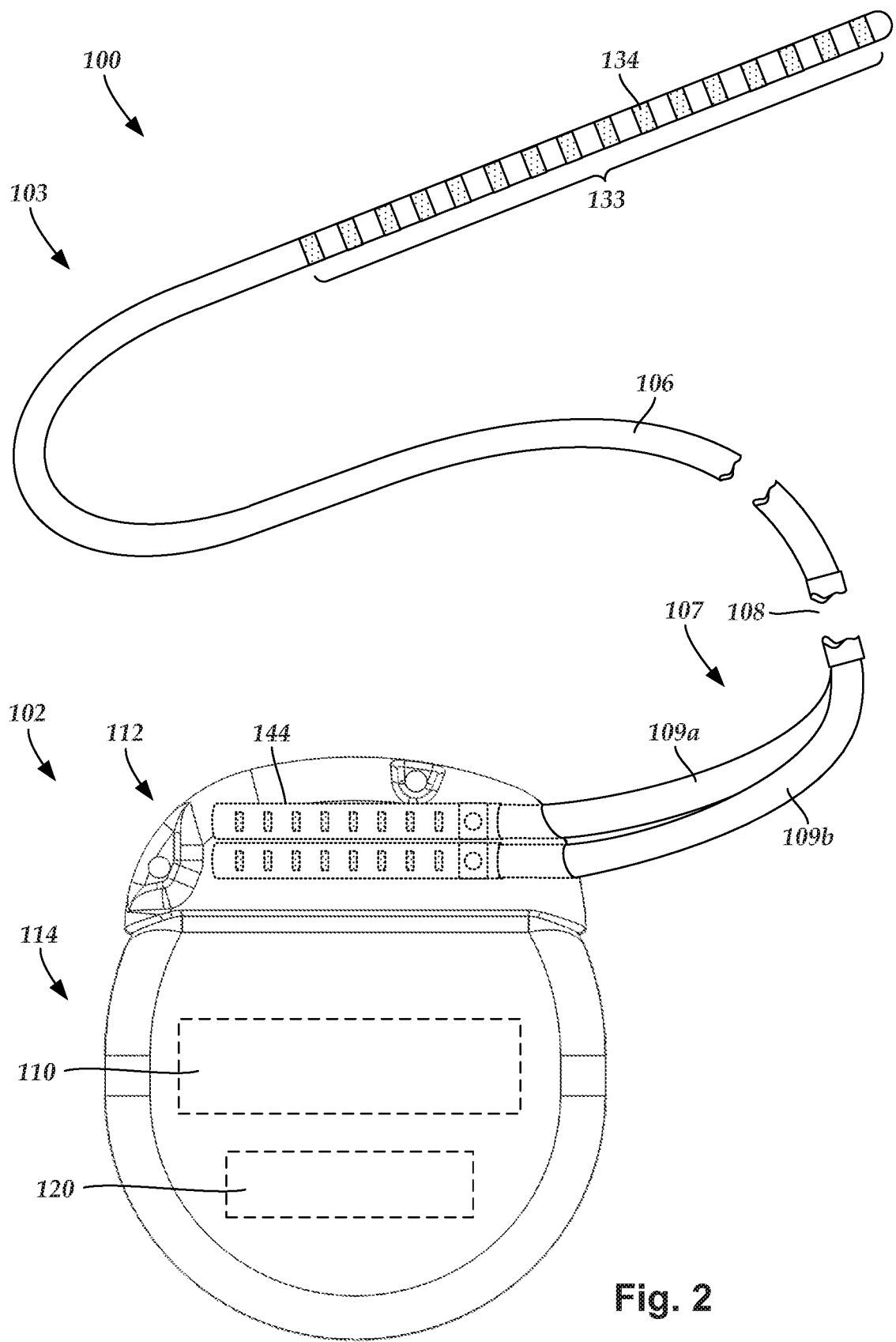
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109*a* and 109*b* configured and arranged to couple to the control module 102 (or another splitter, a lead extension, an adaptor, or the like).

With reference to FIGS. 1 and 2, the control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
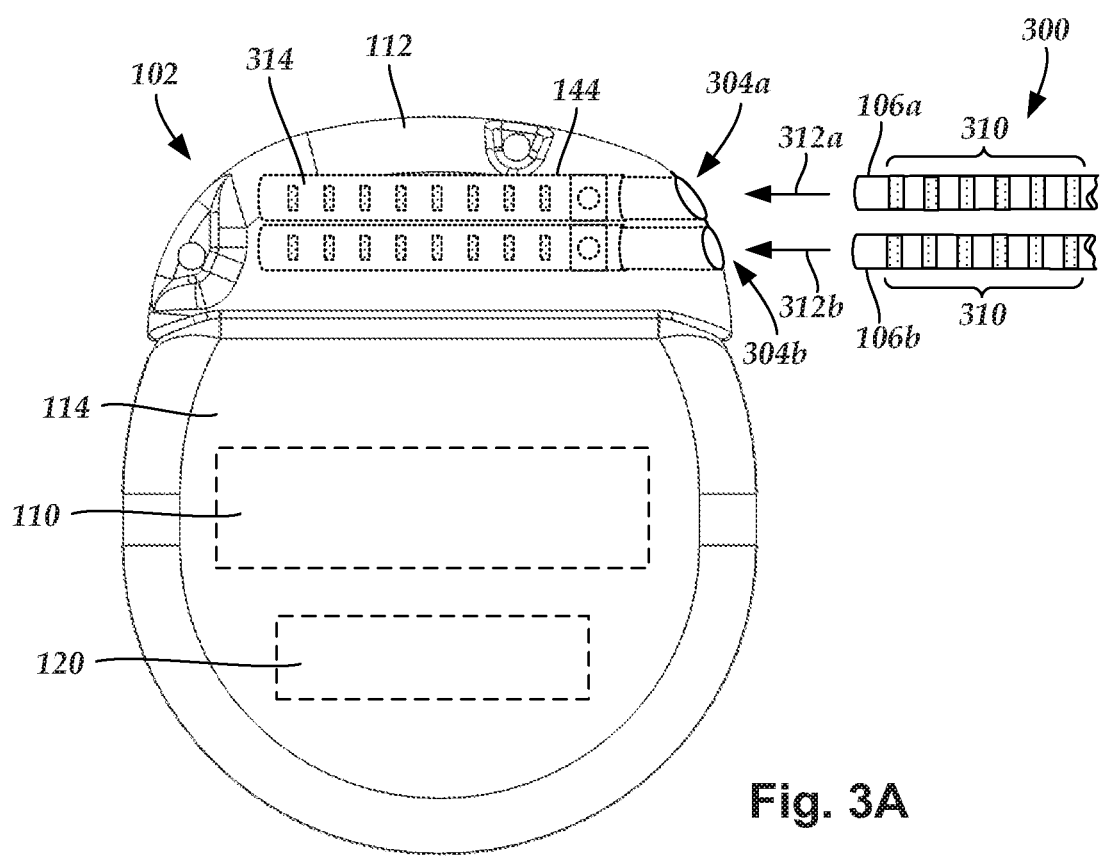
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312*a* and 312*b*. In FIG. 3A (and in other figures), the connector housing 112 is shown having two ports 304*a* and 304*b*. The connector housing 112 can define any suitable number of ports including, for example, one, two, three, four, five, six, seven, eight, or more ports.

The control module connector 144 also includes a plurality of connector contacts, such as connector contact 314, disposed within each port 304*a* and 304*b*. When the elongated device 300 is inserted into the ports 304*a* and 304*b*, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
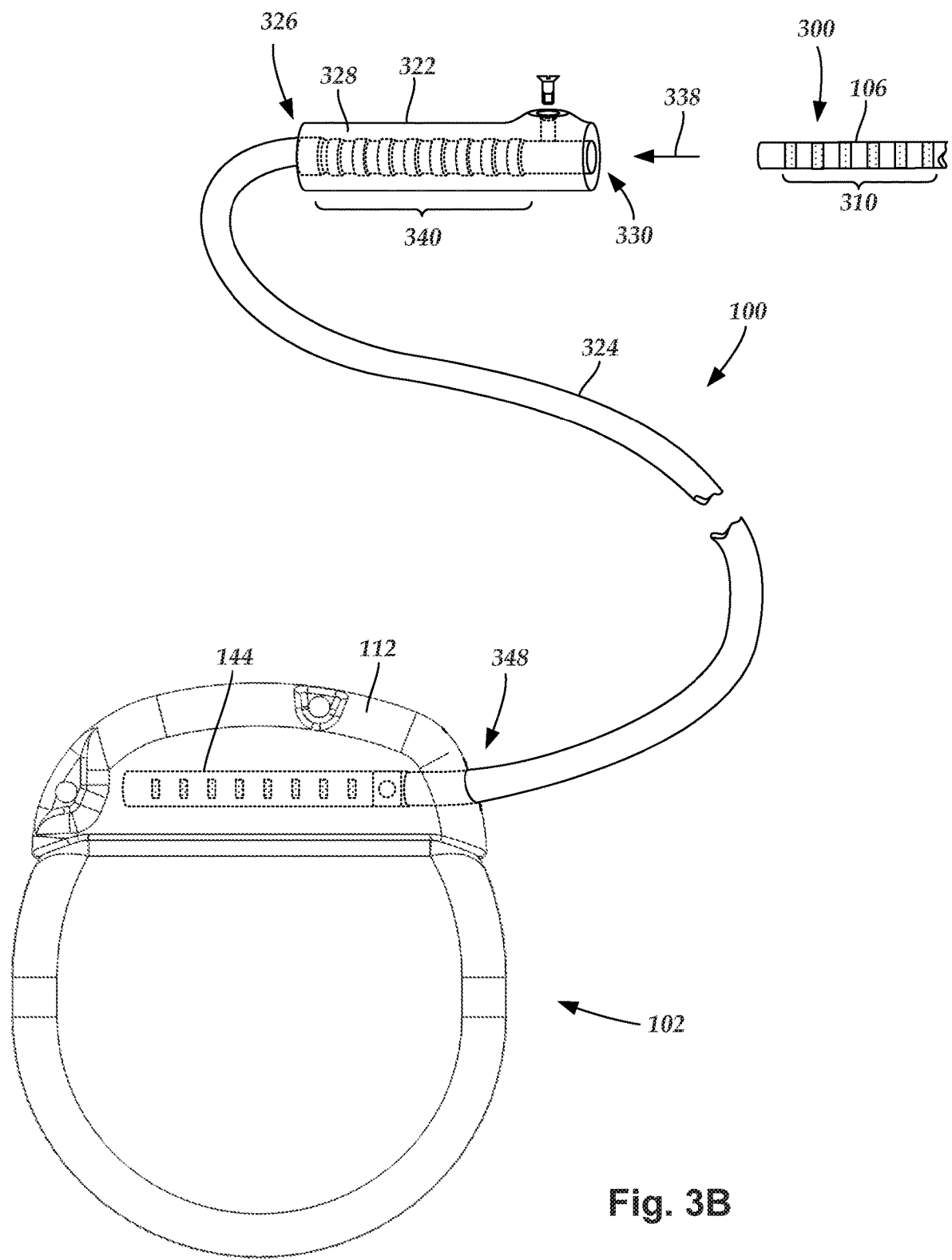
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4:
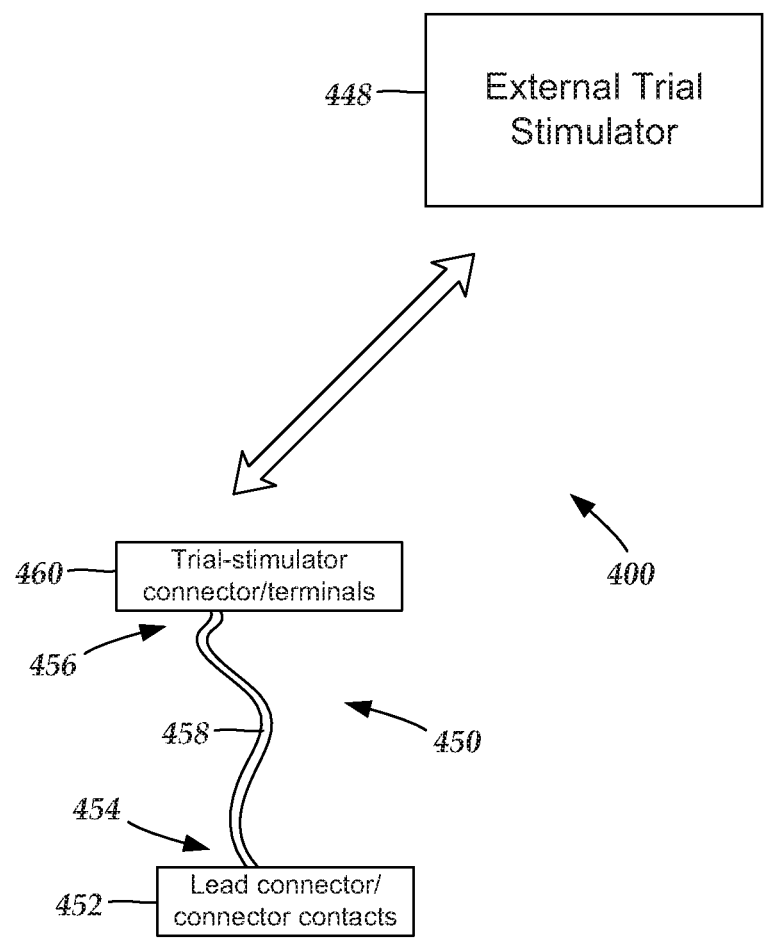
FIG. 4 is a schematic illustration of components of one embodiment of a trial stimulation system, according to the invention.
Figure 4:
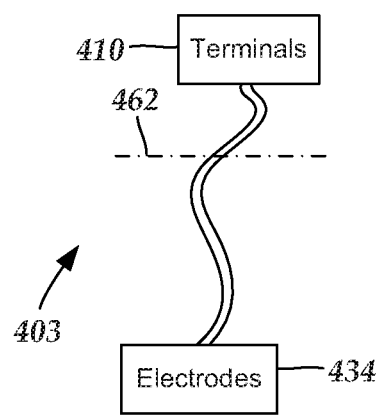

Turning to FIG. 4, during implantation of the lead into a patient it is sometimes desirable to test the positioning or functionality of the electrodes within the patient prior to completion of the implantation. One way to test electrode positioning or functionality is to implant an electrode-including distal end portion of a lead (and, optionally, one or more lead extensions) into the patient. The proximal end portion of the lead (or lead extension) can then be electrically coupled to a trial stimulator that is disposed external to the patient to perform trial stimulations using the electrodes. Once it is determined that the electrodes are properly positioned and functioning within desired parameters, the trial stimulator can be decoupled from the proximal end portion of the lead (or lead extension) and replaced with an implantable control module, and the implantation can be completed.

In some embodiments, the trial stimulations can continue for two, four, six, eight, twelve, or more hours or for one, two, three, four, five or more days. In these instances, the patient may be in a hospital or other care facility. In some embodiments, the trial stimulations may continue for an extended period (e.g., 2-10 days or more) where the patient is sent home with the lead, cable, and trial stimulator to assess the effectiveness of the therapy to determine if a permanent implanted system will be effective in treating the medical condition. During the trial stimulations, the lead can be electrically coupled to the trial stimulator by electrically coupling the proximal end portion of the lead (or lead extension) to an operating room cable ("cable") which, in turn, is electrically coupled to the trial stimulator. In some cases, when multiple leads are implanted into a patient, multiple leads (or lead extensions) may be coupled to the cable.

FIG. 4 is a schematic view of one embodiment of a trial stimulation arrangement 400 that includes a lead 403, a trial stimulator 448, and an operating room cable assembly 450, that couples the lead 403 to the trial stimulator 448. The lead 403 includes an array of electrodes 434 and an array of terminals 410. The terminals 410 are configured and arranged to couple the electrodes 434 to the trial stimulator 448 when the operating room cable assembly 450 is coupled to each of the lead 403 and the trial stimulator 448.

During operation, the electrodes 434 are disposed internal to the patient, while the terminals 410 remain external to the patient, as shown in FIG. 4 by a line 462 schematically representing patient skin. Optionally, the trial stimulation arrangement 400 includes one or more additional devices (e.g., a lead extension, an operating room cable extension, a splitter, an adaptor, or the like or any combination thereof). For example, the trial stimulation arrangement can include a lead extension which is coupleable to, and between, the lead 403 and the operating room cable assembly 450.

The operating room cable assembly 450 includes an elongated body 458 having a first end portion 454 and an opposing second end portion 456, a lead connector 452 with connector contacts, and an optional trial stimulator connector 460 optionally with terminals (a trial stimulator connector and terminals are not needed if the operating room cable assembly is permanently wired, or otherwise permanently attached, to the trial stimulator). Conductors (not shown) extend from the connector contacts of the lead connector to the terminals of the trial stimulator connector. The lead connector 452 is disposed along the first end portion 454 of the operating room cable assembly 450 and the connector contacts within the lead connector are coupleable to the terminals 434 of the lead 403 (or lead extension). The trial stimulator connector 460 is disposed along the second end portion 456 of the operating room cable assembly 450 and is coupleable to the trial stimulator 448, either directly or via one or more operating room cable extensions. Any suitable terminals can be used in the operating room cable assembly including rings, c-shaped contacts, plate contacts, pogo pins, and the like. Examples of terminals can be found in, for example, U.S. Pat. Nos. 7,539,542 and 8,849,396; U.S. Patent Application Publication No. 2013/0098678; and U.S. patent application Ser. No. 14/330,330, all of which are incorporated herein by reference.

Conventionally, the lead connectors of the operating room cable assembly are relatively large, bulky, and heavy. In some instances, conventional lead connectors may require two hands to operate. In some instances, it may not be clear to surgical personnel how to load a lead into the lead connector or how to "lock" the lead within the lead connector.

In the description below, leads will be referred to in connection with the lead connector. It will be understood, however, that a lead extension can be used in place of any of the leads for coupling to the lead connector with a lead coupled, in turn, to the lead extension.

Figure 5A:
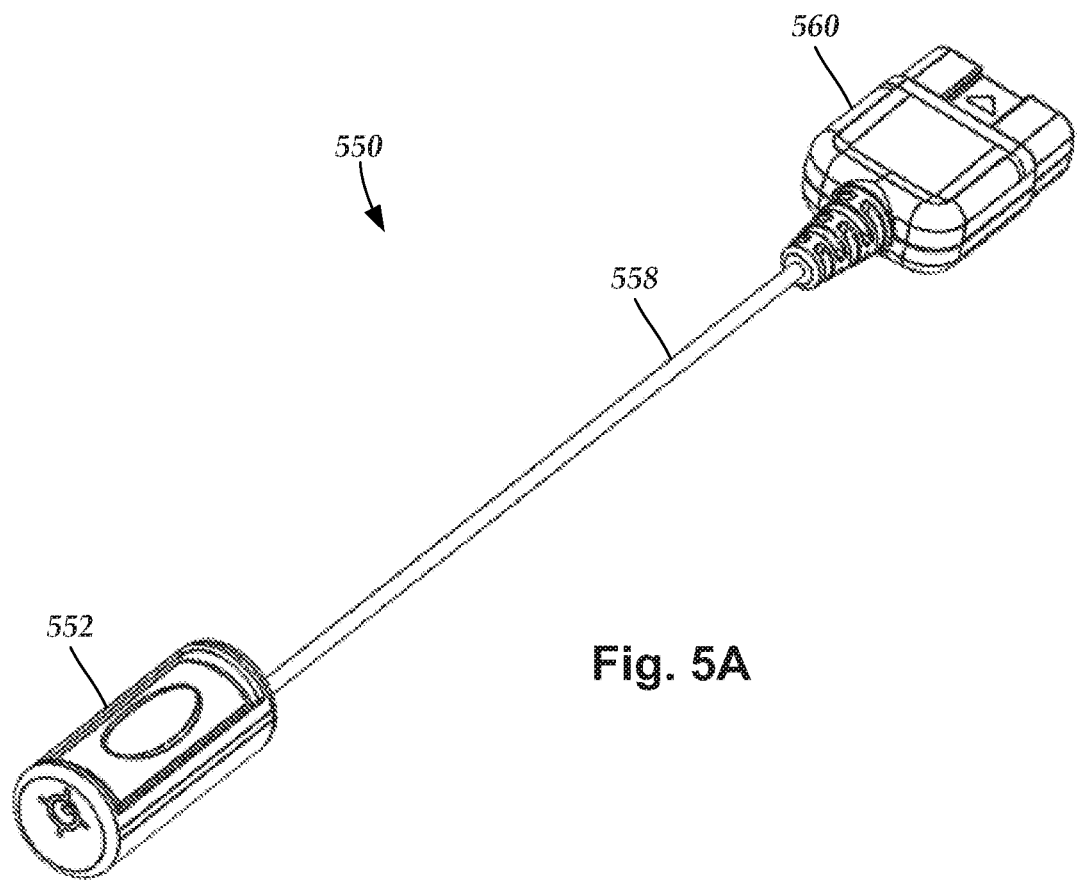
FIG. 5A is a schematic perspective view of one embodiment of an operating room cable assembly, according to the invention.

A lead connector for use with an operating room cable assembly (or as a lead connector on a lead extension) can include a simpler, quicker, and easier locking-unlocking mechanism. One embodiment of an operating room cable assembly 550 with an elongated body 558, a lead connector 552, and trial stimulator connector 560 is illustrated in FIG. 5A. Any suitable trial stimulator connector 560 and elongated body 558 can be used including, but not limited to, those used for conventional or existing operating room cable assemblies. For example, the elongated body may include multiple conductors extending within a non-conductive sheath or jacket. The trial stimulator connector can be any standard or non-standard connector with multiple contacts for connecting to a trial stimulator. Alternatively, the operating room cable assembly 560 is permanently connected to the trial stimulator and does not include a trial stimulator connector.

Figure 5B:
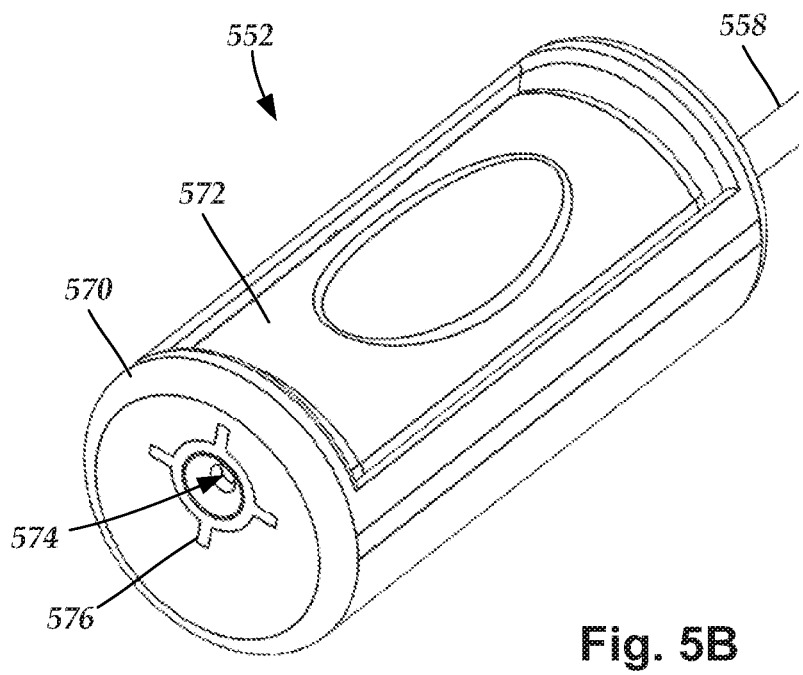
FIG. 5B is a schematic perspective view of a lead connector of the operating room cable assembly of FIG. 5A, according to the invention.
Figure 5C:
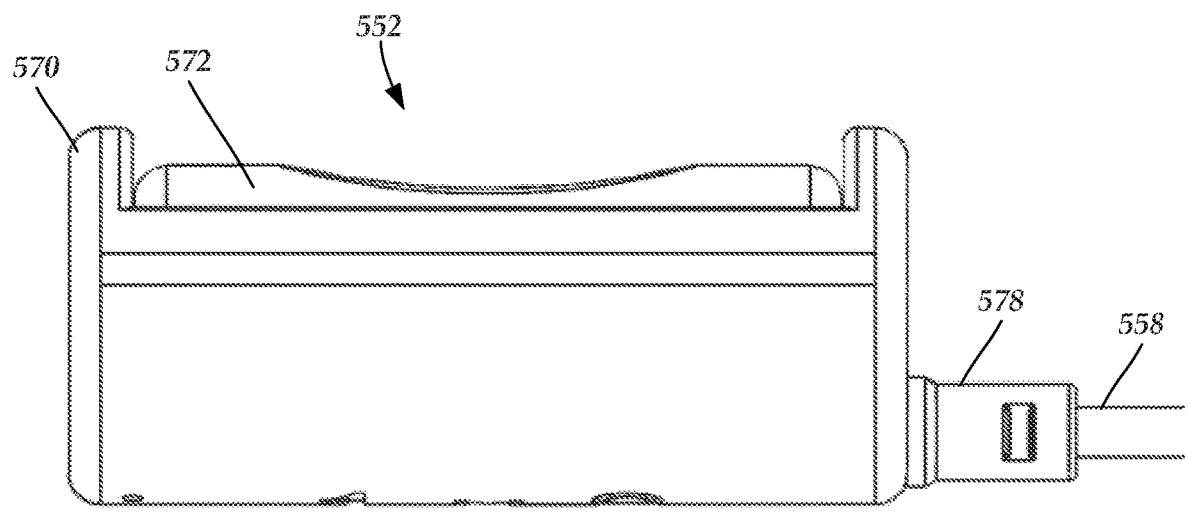
FIG. 5C is a schematic side view of the lead connector of the operating room cable assembly of FIG. 5A, according to the invention.

The lead connector 552, illustrated in close-up views in FIGS. 5B and 5C, includes a housing 570 and a button 572 that can be pushed toward a center of the lead connector to a "load position" (see, FIGS. 5B, 5C, and 6B) for inserting or removing a lead (or lead extension). When the button 572 is released, the button is biased to move away from the center of the lead connector to a "lock position" to lock the lead in the lead connector. The housing 570 includes an opening 574 for insertion of the lead. Optionally, a visually distinctive marking 576 can be placed around the opening 574 to facilitate visual identification of the opening 574 and insertion of the lead. For example, the marking 574 can be in a color distinguishable from the surrounding portions of the housing 570. The elongated body 558 containing conductors extends from the housing 570 and may include a boot 578 to provide stability or prevent breakage at the exit from the housing and may incorporate a strain relief arrangement.

Figure 6A:
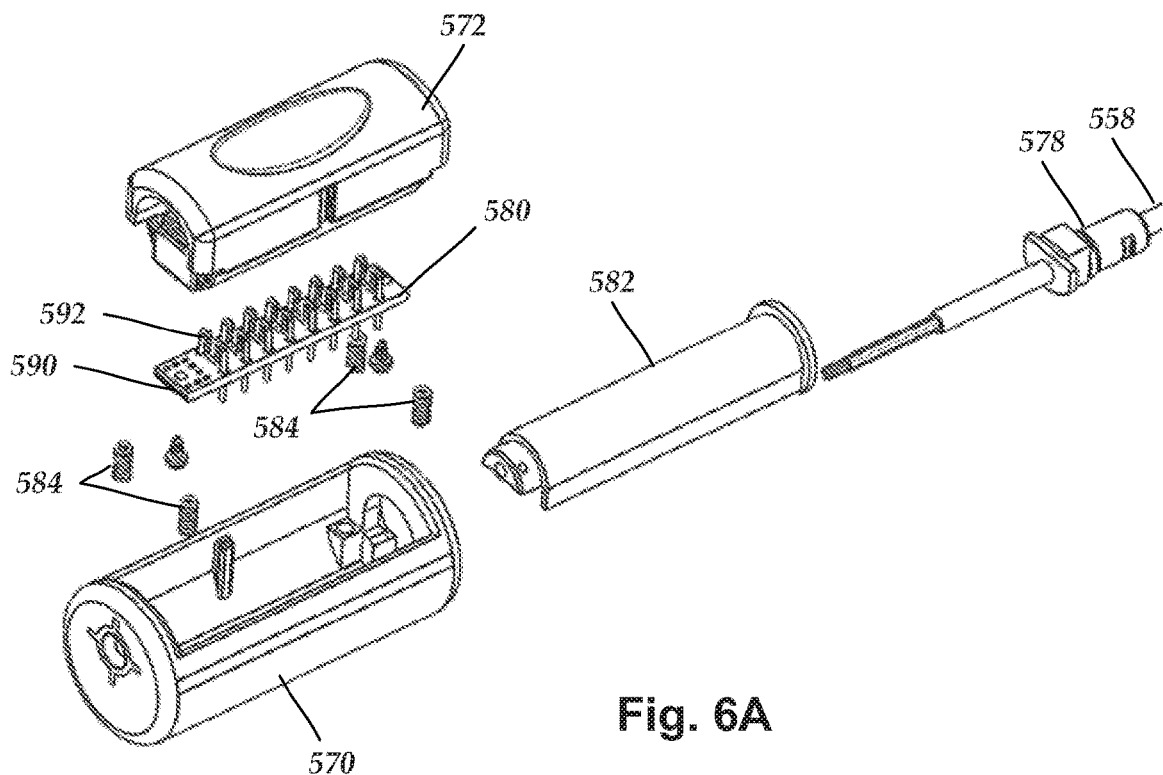
FIG. 6A is a schematic exploded view of the lead connector of the operating room cable assembly of FIG. 5A, according to the invention.
Figure 6B:
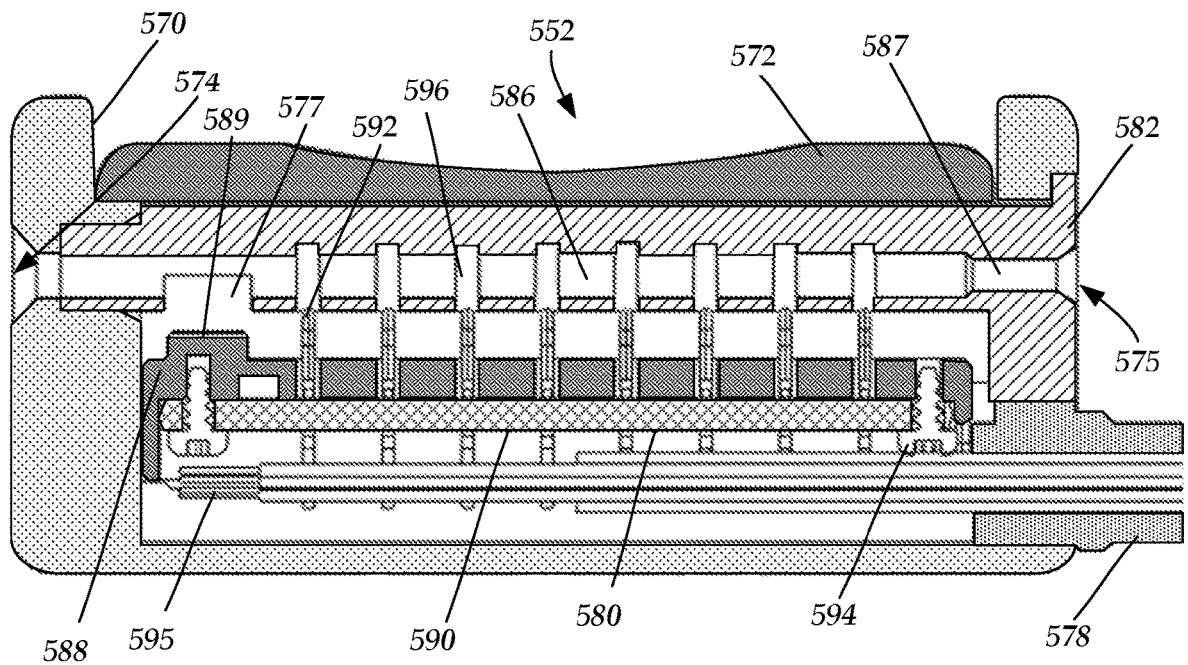
FIG. 6B is a schematic cross-sectional view of the lead connector of the operating room cable assembly of FIG. 5A, according to the invention.
Figure 6C:
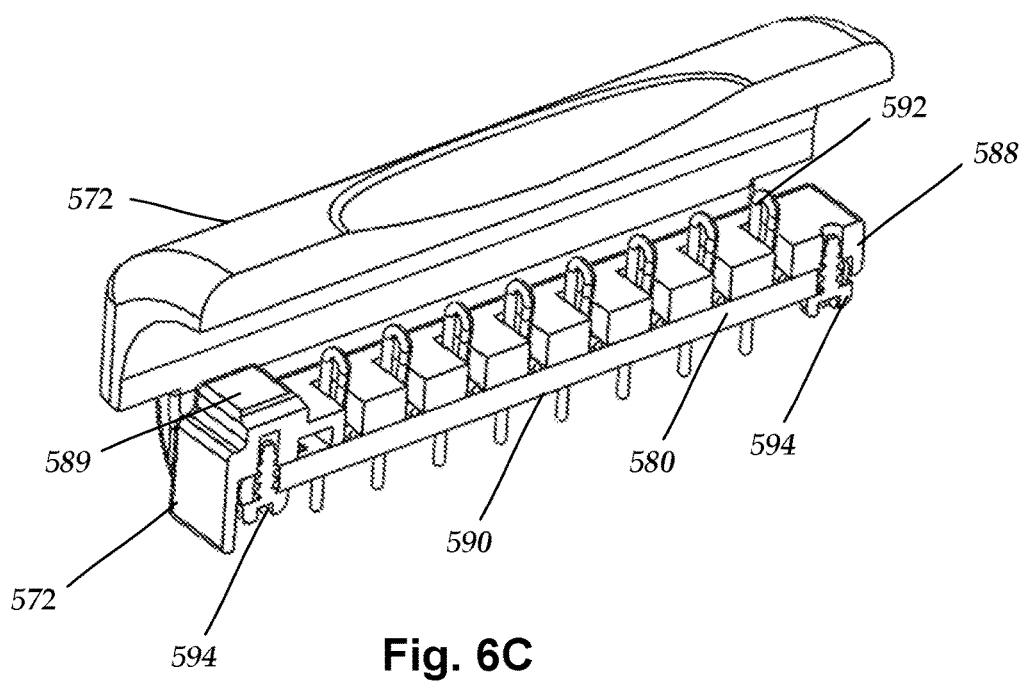
FIG. 6C is a schematic cut-away view of portions of the button, carriage, and contact assembly of the lead connector of the operating room cable assembly of FIG. 5A, according to the invention.

FIG. 6A illustrates an exploded view of one embodiment of the lead connector 552; FIG. 6B illustrates a cross-sectional view of this embodiment in the load position; and FIG. 6C illustrates a cut-away view of a portion (approximately one half) of selected components of the lead connector 552. In addition to the housing 570 and the button 572, the lead connector 570 includes a contact assembly 580, a lead lumen housing 582, and one or more springs 584. The button, 572, housing 570, and lead lumen housing 582 can be made of any suitable material including, but not limited to, plastic materials such as silicone, polyurethane, or the like or combinations thereof. In at least some embodiments, the button, 572, housing 570, and lead lumen housing 582 are made solely of non-conductive materials. In some embodiments, the housing 570 and lead lumen housing 582 are formed as a single piece and, in other embodiments, these two components are separate pieces.

The contact assembly 580 includes a base 590 and multiple contacts 592 attached to the base. The contact assembly 580 is movable relative to the housing 570 and can be moved to a load position for receiving the lead. The contact assembly 580 is biased to a lock position in which the contact assembly the engages a portion of a lead or lead extension within the lead lumen to hold or lock the portion of the lead or lead extension within the lead connector 552.

The base 590 of the contact assembly 580 can be made of any suitable non-conductive material such as, for example, polyimide, epoxy, other printed circuit board materials, flex circuit materials, other plastics, or the like or combinations thereof. The contacts 592 are made of metal or other conductive material and are positioned to engage the terminals of a lead (or lead extension) when the proximal portion of the lead (or lead extension) is properly and fully inserted in the lead connector 570 and the button 572 is in the lock position. As explained further below, the contact assembly 580 is coupled to the button 572 and moves with the button 572 to engage the lead (or lead extension) in the lock position or disengage from the lead (or lead extension) in the load position. Optionally, in the lock position, the contacts 580 may compress or otherwise engage the terminals of the lead to resist removal of the proximal portion of the lead from the lead connector 570.

In the illustrated embodiment, the contacts 592 are "M" shaped pins, but any other suitably shaped contact can be used. Each contact 592 is individually electrically coupled (for example, directly coupled or coupled through a wire) to one of multiple conductors 595 (FIG. 6B) that extend from the lead connector 552 through the elongated body 558 (FIG. 5A) and to corresponding contacts of the trial stimulator connector 560 (FIG. 5A).

As best illustrated in FIG. 6B, the lead lumen housing 582 and the housing 572 define a lead lumen 586 that extends into the lead connector 552 from the opening 574 and is arranged for receiving a proximal end portion of the lead (or lead extension). Optionally, a stylet opening 575 and stylet lumen 587 can also be defined so that a stylet can be inserted through the stylet opening 575 and stylet lumen 587 into the proximal end of the lead (or lead extension). The lead lumen housing 582 and housing 572 also define contact openings 596 through which the contacts 592 can pass as the contacts move from the lock position to the load position and vice versa.

The button 572 includes a carriage 588 to which the contact assembly 580 is attached. Any suitable method of attachment can be used including, but not limited to, screws 594, other fasteners, adhesive, or the like or the carriage 584 and the base 590 of the contact assembly 580 can be formed (e.g., molded) together with, for example, the contacts inserted or otherwise disposed in the combined arrangement. In some embodiments, the button 572 and carriage 588, instead of being a single, integral piece as illustrated in FIG. 6B, can be made of two or more parts that are attached together by fasteners, adhesive, or the like.

In at least some embodiments, the springs 584 (FIG. 6A) reside between the carriage 588 and the housing 570 and urge or bias the contact assembly 580 and the button 572 to the lock position. In some embodiments, the housing 570 may include platforms or receptacles for the springs 584. As the button 572 is pressed to the load position, the contact assembly 580 moves away from the lead lumen 586. When the button 572 is released the springs 584 urge or bias the contact assembly 580 and the button 572 to the lock position with the contact assembly 580 urged toward the lead lumen 586.

Optionally, the carriage 588 includes a lead engagement portion 589 that passes through an opening 577 in the lead lumen housing 582 to engage, or press against, a lead present within the lead lumen 586 to facilitate locking the lead within the lead lumen. The illustrated embodiment has a single lead engagement portion 589, but it will be understood that additional lead engagement portions can be used and may be part of the contact assembly 580 instead of the carriage 588.

Figure 7:
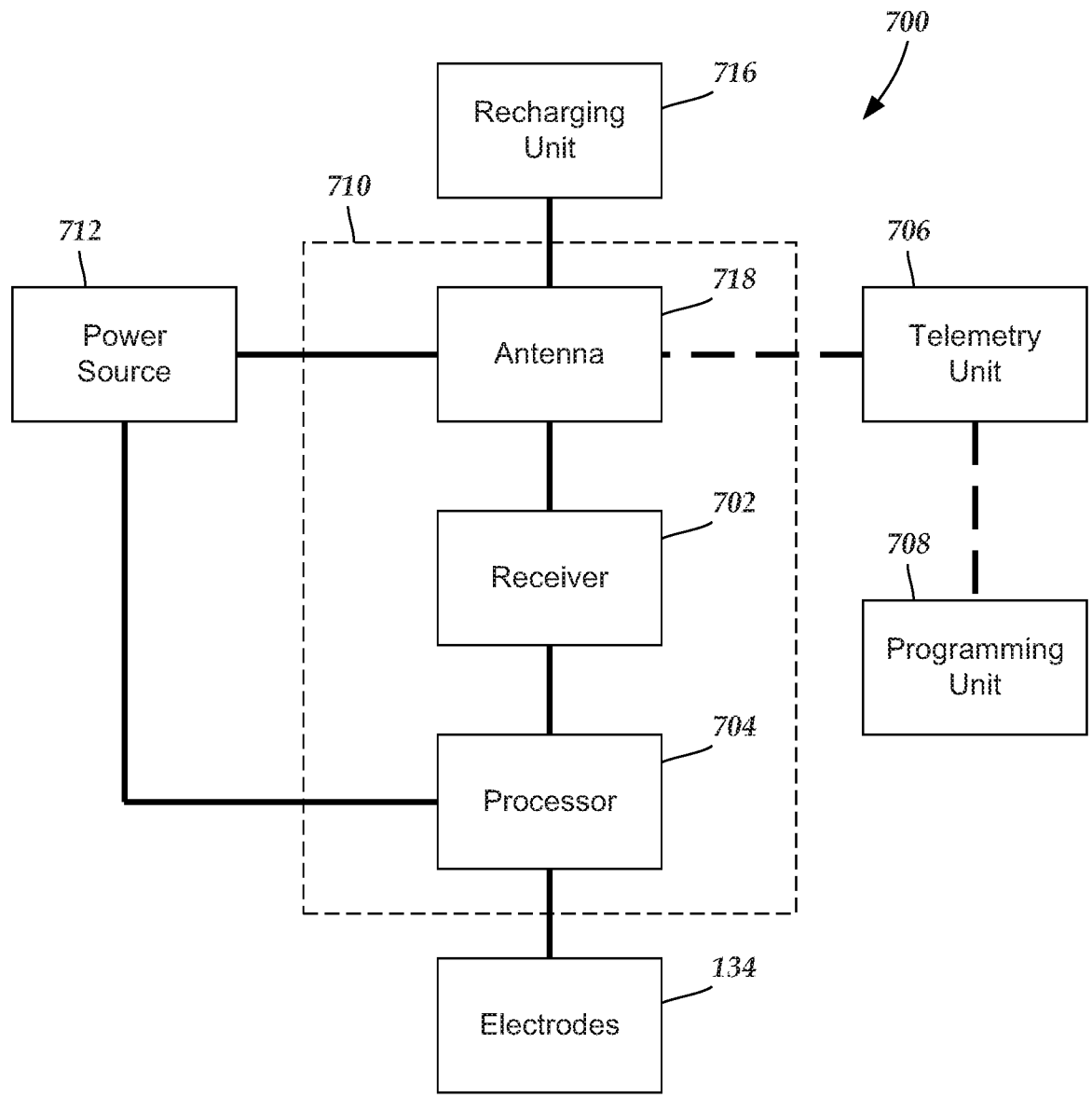
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An operating room cable assembly for an electrical stimulation system, the operating room cable assembly comprising:
   a lead connector comprising
      a housing,
      a lead lumen extending inwardly from a first opening in the housing and configured and arranged to receive a portion of a lead or lead extension,
      a carriage disposed within the housing, and
      a contact assembly disposed on the carriage within the housing and configured and arranged to move with the carriage relative to the housing, wherein the contact assembly and carriage are configured and arranged to move to a load position and are biased to return to a lock position, wherein the contact assembly comprises at least four independent contacts, wherein the contacts of the contact assembly are configured and arranged to engage a portion of any lead or lead extension within the lead lumen when the contact assembly is in the lock position and to disengage from the portion of the lead or lead extension within the lead lumen when the contact assembly is in the load position.

2. The operating room cable assembly of claim 1, further comprising a button coupled to the contact assembly, disposed within the housing, and movable relative to the housing, wherein the button is configured and arranged to move the contact assembly to the load position when the button is pushed and to return the contact assembly to the lock position when the button is released.

3. The operating room cable assembly of claim 1, wherein the contacts are "M" shaped pins.

4. An operating room cable assembly for an electrical stimulation system, the operating room cable assembly comprising:
a lead connector comprising
a housing,
a lead lumen extending inwardly from a first opening in the housing and configured and arranged to receive a portion of a lead or lead extension,
a contact assembly disposed within the housing and configured and arranged to move relative to the housing, wherein the contact assembly is configured and arranged to move to a load position and is biased to return to a lock position, wherein the contact assembly comprises a plurality of contacts, wherein the contacts of the contact assembly are configured and arranged to engage a portion of any lead or lead extension within the lead lumen when the contact assembly is in the lock position and to disengage from the portion of the lead or lead extension within the lead lumen when the contact assembly is in the load position, and
a button coupled to the contact assembly, disposed within the housing, and movable relative to the housing, wherein the button is configured and arranged to move the contact assembly to the load position when the button is pushed and to return the contact assembly to the lock position when the button is released, wherein the button comprises a carriage and the contact assembly is fastened to the carriage.

5. The operating room cable assembly of claim 4, wherein the carriage comprises a lead engagement portion that is configured and arranged to engage the portion of the lead or lead extension in the lead lumen when the contact assembly is in the lock position to facilitate retention of the lead or lead extension.

6. The operating room cable assembly of claim 4, further comprising an elongated body coupled to, and extending from, the lead connector and comprising a plurality of conductors, wherein each of the conductors is coupled to at least one of the contacts of the contact assembly of the lead connector.

7. The operating room cable assembly of claim 6, further comprising a trial stimulator connector coupled to the elongated body and comprising at least one contact coupled to the conductors of the elongated body.

8. A trial stimulation system, comprising:
a trial stimulator; and
the operating room cable assembly of claim 6 coupleable, or coupled, to the trial stimulator.

9. The trial stimulation system of claim 8, wherein the operating room cable assembly further comprises a trial stimulator connector coupled to the elongated body and coupleable to the trial stimulator.

10. The trial stimulation system of claim 8, wherein the elongated body of the operating room cable assembly is permanently attached to the trial stimulator.

11. The trial stimulation system of claim 8, further comprising a lead coupleable to the lead connector of the operating room cable assembly.

12. The trial stimulation system of claim 11, further comprising a lead extension coupleable to the lead and the lead connector of the operating room cable assembly.

13. The operating room cable assembly of claim 4, further comprising at least one spring disposed between the contact assembly and the housing and configured and arranged to bias the contact assembly to the lock position.

14. The operating room cable assembly of claim 4, further comprising a lead lumen housing disposed within the housing and defining at least a portion of the lead lumen.

15. The operating room cable assembly of claim 14, wherein the lead lumen housing further defines a plurality of contact openings that intersect the lead lumen and through which the contacts of the contact assembly can move between the load position and the lock position.

16. The operating room cable assembly of claim 4, further comprising a stylet lumen inwardly extending from a second opening in the housing opposite the lead lumen and intersecting the lead lumen.

17. The operating room cable assembly of claim 4, further comprising a visually distinctive marking disposed on the housing around the first opening.

18. An insertion kit comprising:
the operating room cable assembly of claim 4; and
at least one electrical stimulation lead, each electrical stimulation lead having a distal end portion and a proximal end portion and comprising
a plurality of electrodes disposed along the distal end portion of the electrical stimulation lead,
a plurality of terminals disposed along the proximal end portion of the electrical stimulation lead, and
a plurality of conductors coupling the electrodes to the terminals,
wherein the proximal end portion of the electrical stimulation lead is insertable into the lead connector of the operating room cable assembly.

19. A method for performing a trial stimulation on a patient, the method comprising:
providing the operating room cable assembly of claim 4;
advancing a distal end portion of an electrical stimulation lead into the patient with a proximal end portion of the electrical stimulation lead extending outward from the patient, wherein the distal end portion of the electrical stimulation lead is advanced to a position where a plurality of electrodes disposed along the distal end portion of the electrical stimulation lead are in proximity to a target stimulation location;
placing the proximal end portion of the electrical stimulation lead into the lead connector of the operating room cable assembly while the contact assembly is in the load position; and
allowing the contact assembly to return to the lock position to lock the proximal end portion of the lead in the lead connector.

20. A method for performing a trial stimulation on a patient, the method comprising:
providing the operating room cable assembly of claim 4;
advancing a distal end portion of an electrical stimulation lead into the patient with a proximal end portion of the electrical stimulation lead extending outward from the patient, wherein the distal end portion of the electrical stimulation lead is advanced to a position where a plurality of electrodes disposed along the distal end portion of the electrical stimulation lead are in proximity to a target stimulation location;

coupling the lead to a lead extension;

placing a proximal end portion of the lead extension into the lead connector of the operating room cable assembly while the contact assembly is in the load position; and allowing the contact assembly to return to the lock position to lock the proximal end portion of the lead extension in the lead connector.

* * * * *